US010258579B2

(12) United States Patent
Ciach et al.

(10) Patent No.: US 10,258,579 B2
(45) Date of Patent: Apr. 16, 2019

(54) PROCESS FOR THE PREPARATION OF POLYSACCHARIDE NANOPARTICLES

(71) Applicant: NANOVELOS SP. Z O.O., Warsaw (PL)

(72) Inventors: Tomasz Ciach, Warsaw (PL); Iga Wasiak, Warsaw (PL)

(73) Assignee: NANOVELOS SP. Z O.O., Warsaw (PL)

(*) Notice: Subject to any disclaimer, the term of this patent is extended or adjusted under 35 U.S.C. 154(b) by 142 days.

(21) Appl. No.: 14/485,309

(22) Filed: Sep. 12, 2014

(65) Prior Publication Data

US 2015/0072946 A1    Mar. 12, 2015

Related U.S. Application Data

(63) Continuation of application No. PCT/PL2013/000030, filed on Mar. 12, 2013.

(30) Foreign Application Priority Data

Mar. 14, 2012  (PL) ......................................... 398450

(51) Int. Cl.
| A61K 9/51 | (2006.01) |
| A61K 47/36 | (2006.01) |
| C08B 11/12 | (2006.01) |
| C08B 37/00 | (2006.01) |
| C08B 37/02 | (2006.01) |
| C08B 37/08 | (2006.01) |
| C08L 1/28 | (2006.01) |
| C08L 5/02 | (2006.01) |
| C08L 5/08 | (2006.01) |
| A61K 47/69 | (2017.01) |

(52) U.S. Cl.
CPC .......... *A61K 9/5192* (2013.01); *A61K 9/5161* (2013.01); *A61K 47/36* (2013.01); *A61K 47/6939* (2017.08); *C08B 11/12* (2013.01); *C08B 37/00* (2013.01); *C08B 37/0021* (2013.01); *C08B 37/0072* (2013.01); *C08L 1/286* (2013.01); *C08L 5/02* (2013.01); *C08L 5/08* (2013.01)

(58) Field of Classification Search
CPC ............ A61K 47/48923; A61K 9/5192; A61K 9/5161
USPC ........................... 514/34, 57, 59, 56; 536/6.4
See application file for complete search history.

(56) References Cited

U.S. PATENT DOCUMENTS

| 4,452,773 A * | 6/1984 | Molday .............. A61K 51/1251 210/632 |
| 2006/0013885 A1 | 1/2006 | Nah |
| 2011/0250257 A1* | 10/2011 | Arthur ................ A61L 24/0031 424/443 |

FOREIGN PATENT DOCUMENTS

| EP | 0999222 A1 | 5/2000 |
| EP | 1298145 A1 | 4/2003 |
| WO | 2006082530 A2 | 8/2006 |
| WO | 2007023386 A2 | 3/2007 |
| WO | 2011069475 A2 | 6/2011 |

OTHER PUBLICATIONS

Qu et al. (J. Mater. Chem., 2012, 22(8): 3311-3313).*
International Search Report for International Application No. PCT/PL2013/000030, dated Jul. 4, 2013, with written opinion.
Search Report from the Patent Office of the Republic of Poland for Polish Application No. P.398450, dated Oct. 10, 2012.
Jeanes, Allene and Wilham, C.A., "Periodate Oxidation of Dextran," American Chemical Society Journal, Jun. 1950, pp. 2655-2656, vol. 72.
Lemarchand Caroline, Gref Ruxandra, and Couvreur Patrick, "Polysaccharide-decorated nanoparticles," European Journal of Pharmaceutics and Biopharmaceutics 58, 2004, pp. 327-341, UMRCNRS 8612, School of Pharmacy, Universite Paris, Sud, Chatenay Malabry, France.
Cho Kwangjae, Wang Xu, Nie Shuming, Chen Zhuo (Georgia), and Shin, Dong M., "Therapeutic Nanoparticles for Drug Delivery in Cancer," Clinical Cancer Research, 2008;14, pp. 1310-1316, American Association for Cancer Research.
Mahapatro, Anil and Singh Dinesh K, "Biodegradable nanoparticles are excellent vehicles for site directed in-vivo delivery of drugs and vaccines," Journal of Nanobiotechnology, 2011; 9:55, pp. 1-11.
Zhao, Huiru and Heindel, Ned D., "Determination of Degree of Substitution of Formyl Groups in Polyaldehyde Dextran by the Hydroxylamine Hydrochloride Method," Pharmaceutical Research,1991, pp. 400-402, vol. 8, No. 3, Plenum Publishing Corporation.
Aumeles, A., Serrero A., Durand A., Dellacherie E., Leonard M., "Nanoparticles of hydrophobically modified dextrans as potential drug carrier systems," Colloids and Surfaces B: Biointerfaces 59, Oct. 2007, pp. 74-80.

* cited by examiner

*Primary Examiner* — Shaojia A Jiang
*Assistant Examiner* — Michael C. Henry
(74) *Attorney, Agent, or Firm* — ALGM LLP; Harry J. Guttman

(57) ABSTRACT

A process for the preparation of nanoparticles from polysaccharides and derivatives thereof, by their specific partial oxidation to produce aldehyde groups and attachment of compounds with amino or other group with the R—NH2 bond which react with aldehyde groups, and a nanoparticle produced by such process.

19 Claims, 2 Drawing Sheets

PROCESS FOR THE PREPARATION OF POLYSACCHARIDE NANOPARTICLES

CROSS REFERENCE TO RELATED APPLICATIONS

This application is a continuation under 35 U.S.C. § 120 of International Application PCT/PL2013/000030, filed Mar. 12, 2013, which claims priority to Polish Application PL398450, filed Mar. 14, 2012, the contents of each of which are incorporated by reference herein.

FIELD OF THE INVENTION

The invention provides a process fir the preparation of nanoparticles from polysaccharides and derivatives thereof by specific oxidation of polysaccharide chains and attaching hydrophobic compounds, including medicaments.

BACKGROUND

Conjugates of compounds from the group of polysaccharides and chemical substances which exhibit therapeutic activity and include amino groups are known. For example, WO 2012/004007 discloses conjugates of hydroxyethylated derivative of starch and various medicaments. WO 03/000738 discloses antibiotic/starch conjugates, where the antibiotic is attached to the reducing end of a polysaccharide through a peptide bond. Attachment is Obtained by oxidation of the starch derivative with $I_2$ on its reducing end, in an alkaline aqueous solution, followed by coupling of the oxidized derivative with the antibiotic in an organic solution. Further, from the international application WO03/15826 a pharmaceutical composition is known for inhibiting metastases or preventing recurrence of a malignant cancer, which comprises as an active principle a polysaccharide with a carboxy group linked to an active substance with anticancer activity through amino acid or peptide comprised of 2 to 8 amino acids. The application WO03/074087 pertains to coupling proteins with a starch-derived modified polysaccharide, with the binding interaction between the modified polysaccharide and the protein comprising a covalent bond resulting from a coupling reaction between a terminal aldehyde group of the modified polysaccharide and a functional group of the protein able to react with said aldehyde group. The invention provides also pharmaceutical formulations which include coupled compounds prepared by coupling and use of said compounds for preventive or therapeutic treatment of humans or animals.

From the international application No, WO 2011/069475 a process is known for the preparation of oxidized hyaluronic acid derivatives and a process for modifying such derivatives. According to the process of that application, hyaluronic acid is oxidized with a specific oxidizing agent TEMPO, to obtain an acid derivative with aldehyde groups. The derivative is then used for linking with amines, diamines, amino acids, peptides and other amino-containing compounds. Such linking is implemented by reductive amination with $NaBH_3CN$, in water or a mixture of water and an organic solvent.

The above-mentioned inventions provide couplings (conjugates) of polysaccharides and various kinds of therapeutic substances, however, any of the solutions was aimed at obtaining polysaccharide nanoparticles. Meanwhile, nanoparticles are at present intensively studied as potential carriers for medicaments, due to a number of novel desired properties [Biodegradable nanoparticles are excellent vehicle for site directed in-vivo delivery of drugs and vaccines, Mahaparto A., Singh K., Journal of Nanobiotechnology, 9, 2011]. Nanoparticles with diameters of about 50 nm to about 200 nm, having suitable surface properties, could circulate for a long time in the blood avoiding elimination by kidneys, liver or spleen filtration (long circulating particles, stealth particles). The surface of such nanoparticles should induce neither a response of the immune system nor aggregation of small plasma proteins—opsonins. In that instance, a surface of hydrogel properties, as created by highly hydrophilic polymers such as polyethylene glycol, polysaccharides, polyvinyl alcohol, is particularly desirable. Polysaccharides are especially desirable due to their frequently natural origin, biodegradability and similarity to substances occurring in the body. Such long-circulating nanoparticles tend to accumulate in areas of tumors or inflammations (passive targeting) [Therapeutic Nanoparticles for Drug Delivery in Cancer, Kwangjae Cho, Xu Wang, Shuming Nie, Zhuo Chen, Dong M. Shin, Clin. Cancer Res., 2008 14; 1310]. The effect is due to the fact that cell membranes of endothelial cells padding the circulatory system are tightly sealed by appropriate proteins and a gap between them is several nanometers wide. In the tumor or inflammation area the gaps are much wider and reach several hundred nanometers. This makes the nanoparticles accumulate in the gaps and "leak" from the circulation into the surrounding afflicted tissue, including the tumor. Such passive accumulation of nanoparticles in the disease afflicted area allows for an increased drug concentration in the areas, enhances efficacy of the treatment and reduces side effects. Additional feature of the nanoparticles is their ability to be surface-modified with suitable proteins, metabolites or antibodies to exhibit active affinity to specific cell types, including tumor cells. This allows delivery of medicaments primarily to the afflicted cells, it is desirable to prepare the surface of nanoparticles from polysaccharides due to the fact that tumor cells exhibit significantly increased demand for glucose (the Warburg effect) which in turn allows obtaining an increased affinity of polysaccharide nanoparticles to tumor cells. Such polysaccharide nanoparticles with a drug would penetrate more efficiently the cancer cells and kill them, and when labeled with fluorescent marker, they become an efficient diagnostic tool. Another important application of nanoparticles is gene therapy. A nanoparticle containing a RNA or DNA fragment is able to penetrate a cell and influence the gene-reading processes occurring in the cell. Hope arises to heal genetic diseases.

There are numerous methods for preparation of nanoparticles, but unfortunately most of them are very complex and require application of drastic conditions (ultrasounds, high temperatures), aggressive chemical compounds, toxic organic solvents or surface-active compounds [Biodegradable nanoparticles are excellent vehicle for site directed in-vivo delivery of drugs and vaccines, Mahaparto A., Singh K., Journal of Nanobiotechnology, 9, 2011]. Nanoparticles for therapeutic use should be non-toxic and most preferably biodegradable. Polysaccharides make a very good material for the preparation of such nanoparticles, due to their biocompatibility and biodegradability [Lemarchand C., R. Gref, P. Couvreur, Polysaccharide-decorated nanoparticles, European Journal of Pharmaceutics and Biopharmaceutics 58, 2004]. However, known methods for the preparation of nanoparticles from polysaccharides by attaching hydrophobic groups are complex and require use of surface-active materials or aggressive chemicals [Nanoparticles of hydrophobically modified dextranes as potential drug carier system, Aumelas A., Serrero A., Durand, E., Dellacherie E., Leonard M., Colloids and Surfaces B, 59, 2007]. Nanoparticles such prepared must be further purified for a long period of time as a consequence of toxic properties of the compounds.

SUMMARY

The invention was directed to a process tier the preparation of polysaccharide nanoparticles in mild conditions, to allow for covalent bonding of therapeutic compounds which are sensitive to aggressive environment.

The process for the preparation of nanoparticles from polysaccharides and derivatives thereof, by their specific partial oxidation to produce aldehyde groups and attach compounds with amino or other group with the R—$NH_2$ bond which react with aldehyde groups of the invention is characterized in that the polysaccharide or derivative thereof is oxidized by a known method to give aldehyde groups until the oxidation degree of 0.1% to 80% of the sugar rings is obtained, then at least one nanoparticle-forming agent, which is an organic chemical compound with a R—$NH_2$ bond that after attachment of the aldehyde group exhibits hydrophobic properties, and at least one active substance comprising at least one R—$NH_2$ or N—H bond is added to the solution of the oxidized polysaccharide in water or a mixture of water and an organic solvent, the reaction being conducted at the pH of the solution of 1 to 9, at the temperature of 10 to 100° C., most preferably 20-60° C., where the total molar ratio of amine groups to aldehyde groups is from 20 to 0.5. The nanoparticle-forming agent is selected from a group comprising: aliphatic or aromatic organic amines comprising from 4 to 20 carbon atoms, amides and hydrazides of aliphatic and aromatic organic acids comprising from 4 to 20 carbon atoms, hydrophobic amino acids, phosphatidylethanolamine, The active substance contains an amino, amido or hydrazide group.

The nanoparticle-forming agent can be added simultaneously with the active substance or after the active substance is added. It is preferable to add the active substance first, since the reaction occurs slower after the nanoparticles are folded resulting possibly in incomplete addition of the active substance and loss thereof in the purification of the product. Sometimes, the active substance could be accumulated in the nanoparticles in the nanocrystal forms precipitated in hydrophobic areas created by the folding agent, and then it is not covalently, but physically bound and could be added in greater amounts. This is the case when it is poorly water-soluble around neutral pH, and well soluble at pH lower than 7.

Both forming agent and the active substance is preferably introduced in the form of salts that are readily water-soluble, e.g. hydrochlorides. If amine is introduced as the more readily soluble salt (e.g. hydrochloride), pH lowers in the course of the reaction, and the solution is then slowly neutralized with the aqueous base solution, The optimal pH is dependent on alkalinity of the amine employed. Generally, the increase in the hydrogen ion concentration activates the aldehyde group, but also results in the drop in concentration of the free non-protonated amine; the optimal pH of the first order reaction lies between 4 and 6, further increase in pH allows to complete the process by decreasing the amine cation concentration.

The process for the preparation of nanoparticles could also be conducted in organic or mixed solvents, such as water/DMSO, water/acetonitrile, water/ether. To increase resistance to hydrolysis of the obtained nanoparticles, reduction of the formed bonds with $NaBH_4$ or $NaBH_3CN$ is utilized, also in the aqueous solution and under mild conditions.

Preferably, as a nanoparticle-forming agent the following are employed: butylamine, pentylamine, hexylamine, octylamine, decylamine, dodecylamine, tetradecylamine, hexadecylamine, cyclohexylamine, benzylamine, ethylphenylamine, sphingosines, oleic acid amide, palmitic acid amide, stearic acid hydrazide, palmitic acid hydrazide, oleic acid hydrazide, leucine, isoleucine, valine, methionine, alanine, phenylalanine or cephalin (phosphatidylethanolamine). It is preferable to add the forming agent as an aqueous solution of an amine salt, for example hydrochloride, nitrate or sulfate, since salts of the instant amines are usually better soluble in water.

Preferably, as an active substance comprising amino, amido or hydrazide group drugs are used which contain such groups, such as daunorubicin, doxorubicin, aminoacridins and derivatives thereof (like amsacrine), cisplatin and derivatives thereof, methotrexate, cytarabine, gemcitabine, dapsone, acyclovir, azidothymidine, 5-fluorouracil, mercaptopurine, imatinib, sunitinib, bleomycin, actinomycin, mitomycin, dactinomycin, melphalan, temozolomide, celecoxib, nelarabine, cladribine, isoniazid or derived medicaments, where a carboxy group was converted into amide or hydrazide; RNA or DNA fragments suitable for gene therapy, or derivatives thereof; plain and fluorescent dyes such as 9-aminoacridine and other acridine dyes, DAPI, rhodamine and derivatives thereof, neutral red, trypan blue. It is preferable to add the active substance into the reaction medium as an aqueous solution of an amine salt, for example hydrochloride, nitrate or sulfate, salts of the instant amines are usually better water-soluble. If such an active substance dissolves in water in the acidic environment, but it is poorly soluble in the neutral environment, said substance could be bound within nanoparticles solely by physical interactions. On increase of it will precipitate within hydrophobic areas of nanoparticles as nanocrystals.

Preferably, as a polysaccharide, the polysaccharide is used which is soluble in water or other solvents, of the molecular weight up to 1000 kDa, most preferably dextran, starch and derivatives thereof (hydroxyethylstarch), amylose and derivatives thereof, cellulose derivatives (hydroxyethylcellulose, hydroxypropylcellulose, carboxymethylcellulose), glycogen, hyaluronic acid, heparin, alginic acid, carrageen.

Preferably oxidation is carried out up to the degree of oxidation of 0.5% to 80% of the oxidized sugar rings in the polysaccharide.

Preferably oxidation is carried out with the participation of the oxidation agent, which comprises periodate ions (e.g. sodium or potassium periodate), salts of lead with the oxidation number of 4, compounds of copper with the oxidation number of 2 or water oxidized in the presence of suitable catalysts such as e.g. vanadium oxides.

Moreover, the obtained nanoparticles could be modified with antibodies or peptides, or proteins, also by reaction of aldehyde groups of the oxidized polysaccharide with amine groups of peptides.

The aqueous suspension of nanoparticles thus obtained is purified by dialysis, precipitation, contrifugation, or employed directly. The obtained solution of nanoparticles could be lyophilized. For lyophilization, a substance could be added which plays a role of a protecting agent (cryoprotectant), such as a non-modified polysaccharide—e.g. dextran. The obtained nanoparticles display self-organizing capabilities, if lyophilized to a dry powder, after suspending in water or saline, form nanoparticles in several minutes.

DETAILED DESCRIPTION OF THE PREFERRED EMBODIMENTS

Figure 1:
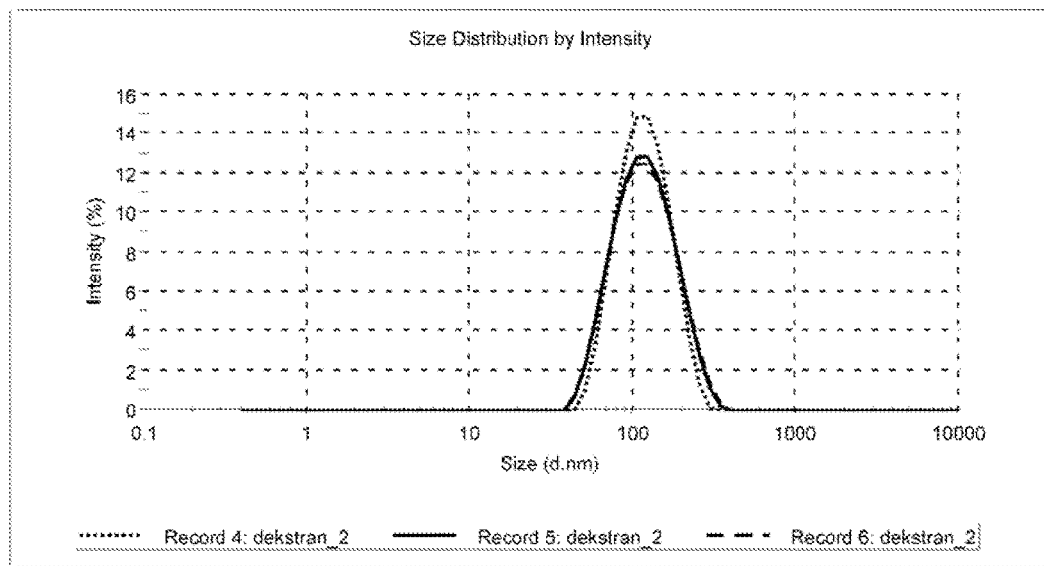
FIG. 1 shows a distribution of diameters of nanoparticles obtained under the method of Example 1.

According to the invention, a polysaccharide is pre-oxidized in an aqueous solution by adding a predetermined amount of an oxidizing agent. In the course of the specific oxidation, monosaccharide, e.g. glucose rings are cleaved rather than the polysaccharide chain, and oxidized rings form aldehyde groups. This is one of the typical specific oxidation reaction employed in organic chemistry, as exemplified by a process of mono or polysaccharide oxidation with periodates. [Jeanes, Ailene and William, C. A. Periodate Oxidation of Dextran, Journal of American Chemical Society 72.6, (1950): 2655-2657]. In the oxidation process, a carbon-carbon bond is cleaved which has —OH groups on the adjacent carbons and aldehyde groups form on the both ends formed. Other methods of partial oxidation could be also employed which lead to formation of aldehyde groups along the polysaccharide chain by cleavage of monosaccharide (glucose) rings and proceeding without cleaving the polysaccharide chain. The degree of oxidation—a number of aldehyde groups can be determined in a known manner; for example by reacting aldehydes with hydroxylamine hydrochloride and titrating the liberated hydrochloric acid [Zhao, Huiru, Heindel, Ned D., Determination of Degree of Substitution of Formyl groups in Polyaldehyde Dextran by the Hydroxylamine Hydrochloride Method, Pharmaceutical Research, 8.3 (1991):400-402]. To the prepared polysaccharide molecules, forming compounds are attached by reacting aldehyde groups with amino groups, which leads to spontaneous formation of nanoparticles.

According to the invention, the oxidized polysaccharide is simultaneously modified by at least two kinds of substances with the nature of amine: nanoparticle forming agent(s) hydrophobic by nature, with remaining substances being therapeutic agents or colorants, while it is possible to use in one nanoparticle at the same time several various active substances. This allows to obtain synergetic effect of combined activities of several medicaments. The simultaneous use of several medicaments significantly decreases the possibility of developing drug resistance by the tumor and enables active destruction of a cell regardless of the cell cycle phase. In the process of the invention, due to hydrophobic-hydrophilic interactions the polysaccharide nanoparticle is formed that contains the active substance and the hydrophobic folding agent inside, and its outer layer comprises hydrophilic components, mainly the polysaccharide. It is also possible to simultaneously modify the polysaccharide with the forming agent, the drug(s) and aldehyde group-reactive component which enhances affinity to specific cell types, such as antibodies, nucleotide bases or metabolites, for example folic acid. On formation of nanoparticles, the hydrophobic agents get inside, and the hydrophilic ones are positioned outside the nanoparticles.

The reaction of the invention proceeds in the aqueous environment, under the mild temperature conditions and without organic solvents or surfactants. The obtained nanoparticles are non-toxic as such (if prepared without a toxic drug) and could be used as carriers for medicaments and color or fluorescent indicators, in the therapy and diagnostics of tumors in particular. The nanoparticles may contain one or more forming agents or several drugs in various combinations, and they may also contain adjuvants (diindolylmethane), that advance their efficiency as medicaments.

The stability of the prepared macromolecules is usually sufficient and reaches from several to over a dozen weeks in the aqueous environment. The dry stability after lyophilization is markedly higher and exceeds a year with proper storage. The stability of the bond formed between amino and aldehyde groups could be additionally enhances by reducing aldehyde—amine bond.

The process of the invention was illustrated in more detail in the working examples.

EXAMPLE 1

Dextran of the molecular weight 70 kDa was oxidized with sodium periodate to oxidize about 5% of glucose rings, and purified. To conduct it, an aqueous dextran solution was prepared and sodium periodate added thereto. Stoichiometry of the reaction depends on oxidation conditions, a molecular weight, and, frequently, the origin of dextran, and equals to from 1 to 2 moles of periodate per a mole of oxidized glucose (two aldehyde groups formed), and has to be verified experimentally. The process of dextran oxidation was conducted at the room temperature in a vessel made of dark glass for one hour. Then, the solution was neutralized and purified by dialysis against distilled water, followed by stripping water in vacuo. The number of aldehyde groups was determined by the known hydroxylamine titration method. 5% solution of said dextran in distilled water was prepared. Then, daunorubicin hydrochloride at 15 mol % based on the number of moles of aldehyde groups in the used amount of oxidized dextran was added. The solution was stirred for 20 minutes at 30° C. Then, the 5% aqueous dodecylamine hydrochloride solution was added at 85 mol % based on the initial number of moles of aldehyde groups in the used amount of oxidized dextran and the temperature was raised to 35° C., and the reaction was continued for 60 minutes. The running reaction causes lowering pH of the reaction environment. Then, raising of pH was started by adding 5% aqueous NaOH solution. Adding was conducted in a manner to raise pH to pH 9 in 30 minutes. After pH=9 was reached, the reaction was continued for additional 30 minutes. Alanine was then added at 15 mol % based on the initial number of moles of aldehyde groups in the used amount of oxidized dextran, to bind all unreacted aldehyde groups. After 15 minutes of stirring, the solution was neutralized with 5% hydrochloric acid to pH=7 and purified by dialysis for 24 hours. Then, 20 weight % (based on the initial weight of oxidized dextran) of pure non-oxidized dextran was added as a cryoprotectant and the solution was lyophilized. The powder was resuspended in water to give a suspension of nanoparticles. The distribution of diameters of the obtained nanoparticles was measured with the Malvern Zeta Sizer apparatus shown on FIG. 1. Measurements made with the NanoSight apparatus with a 405 nm laser revealed the slightly lower mean particle diameter and the narrower diameter distribution.

EXAMPLE 2

Figure 2:
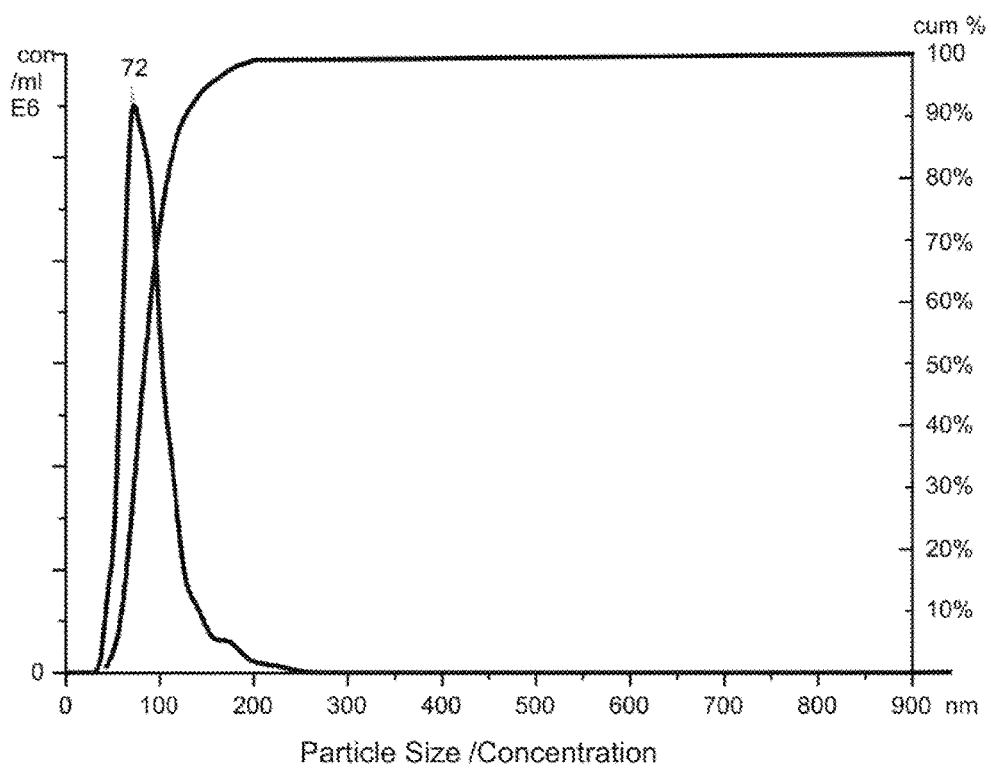
FIG. 2 shows a distribution of diameters of nanoparticles obtained under the method of Example 2.

Dextran of the molecular weight 40 kDa was oxidized with sodium periodate to oxidize about 20% of glucose rings, and purified. A 10% solution of such dextran in distilled water was prepared. Then, doxorubicin hydrochloride at 20 mol % based on the number of moles of aldehyde groups in the used amount of oxidized dextran was added. The solution was stirred for 20 minutes at 30° C. Then, the 5% aqueous octylamine hydrochloride solution was added at 80 mol % based on the initial number of moles of aldehyde groups in the used amount of oxidized dextran, and the temperature was raised to 40° C., and the reaction was continued for 60 minutes. The running reaction causes pH lowering. Then, raising of pH was started by adding 5% aqueous NaOH solution. Adding was conducted in a manner to raise pH to pH 8 in 30 minutes. After pH=8 was reached, the reaction was continued for additional 30 minutes. Alanine was then added at 10 mol % based on the initial number of moles of aldehyde groups in the used amount of oxidized dextran. After 15 minutes of stirring, the solution was neutralized with 5% hydrochloric acid to pH=7 and NaBH$_3$CN was added in 10 mol % excess based on the initial amount of aldehyde groups. Then, the reaction was carried out for 12 hours. The solution was neutralized and purified by extensive dialysis for 48 hours, then dextran was added at 50 weight % based on the initial weight of dextran and the solution lyophilized. After resuspending in water, the distribution of diameters of the obtained nanoparticles was measured with the NanoSight apparatus with a 405 nm laser and shown on FIG. 2.

EXAMPLE 3

A 4% aqueous solution of carboxymethylcellulose of the molecular weight about 100 kDa and the oxidation number of 5% was prepared, and pH was adjusted to pH 5. Then, 9-aminoacridine was added as its aqueous hydrochloride solution at 50 mol % based on the initial amount of aldehyde groups of the cellulose derivative used. Then, aqueous octylamine was added at 55 mol % based on the initial number of moles of aldehyde groups. The reaction was carried out at 40° C. for one hour. Then the solution was neutralized by raising pH to pH 9 in 15 minutes, left for 30 minutes and dialyzed. The fluorescent nanoparticles were obtained with the 150 nm mean diameter.

EXAMPLE 4

Dextran of the molecular weight of 70 kDa was oxidized with sodium periodate to oxidize about 15% of glucose rings, and purified. A 10% solution of such dextran in distilled water was prepared. Then, doxorubicin hydrochloride at 25 mol % based on the number of moles of aldehyde groups in the used amount of oxidized dextran was added. The solution was stirred for 20 minutes at 35° C. Then, folic acid was added at 5 mol % based on the initial amount of aldehyde groups to enhance affinity of nanoparticles to tumor cells. After 15 minutes, the 5% aqueous isoleucine hydrochloride solution was added at 80 mol % based on the initial number of moles of aldehyde groups in the used amount of oxidized dextran, and the temperature was raised to 40° C., and the reaction conducted for 60 minutes. Then, raising of phi was started by adding the 5% aqueous NaOH solution. Adding was conducted in a manner to raise pH to pH 9,5 in 30 minutes. The reaction was continued for additional 30 minutes. Then the solution was neutralized and purified by dialysis for 24 hours. The mean diameter of the obtained nanoparticles was 140 nm.

EXAMPLE 5

The carboxymethylcellulose sodium salt was oxidized in the aqueous solution with hydrogen peroxide in the presence of tetra-sulfo iron-phthalocyanine catalyst [Weber, et al, Complexes derived from strong field ligands . . . , Inorganic Chemistry, 1965, 4, 469-471]. The process was conducted for 12 hours at 40° C., then the product was purified by filtration, followed by dialysis. The amount of aldehyde groups in the obtained aldehyde carboxymethylcellulose derivative was determined by the known hydroxylamine titration method. The 5% solution of the obtained derivative in distilled water was prepared. Then, doxorubicin hydrochloride at 10 mol % based on the number of moles of aldehyde groups in the used amount of oxidized dextran was added. The solution was stirred for 20 minutes at 30° C. Then, the 5% aqueous dodecylamine hydrochloride solution was added at 90 mol % based on the initial number of moles of aldehyde groups in the used amount of oxidized dextran and the temperature was raised to 35° C., and the reaction was continued for 60 minutes. Then, raising of pH was started by adding 5% aqueous NaOH solution. Adding was conducted in a manner to raise pH to pH 9 in 30 minutes. After pH=9 was reached, the reaction was continued for additional 30 minutes. Alanine was then added at 30 mol % based on the initial number of moles of aldehyde groups in the used amount of oxidized dextran, to bind all unreacted aldehyde groups. After 15 minutes of stirring, the solution was neutralized with 5% hydrochloric acid to pH=7 and purified by dialysis for 24 hours. The mean diameter of the obtained nanoparticles as measured with the Malvern Zeta Sizer apparatus was 110 nm.

EXAMPLE 6

The 1% aqueous hyaluronic acid sodium salt solution was prepared and oxidized with sodium periodate to the degree of oxidation of 5% as in Example 1. The pH was adjusted to pH 5, daunorubicin hydrochloride and cytarabine hydrochloride were added for the each drug comprising 10 mol % of all aldehyde groups of oxidized hyaluronic acid, and the reaction was conducted for 15 minutes at 30 degrees. Then, aqueous decylamine hydrochloride solution was added at 85 mol % based on the initial number of moles of aldehyde groups. The reaction was conducted at 40° C. for one hour. Then, pH was raised to pH do 9 within 20 minutes, the solution was neutralized and dialyzed. An aqueous suspension of polysaccharide nanoparticles was obtained comprising two drugs with distinct mechanisms of action.

What is claimed is:
1. A process for producing polysaccharide nanoparticles in an aqueous suspension, comprising:
A) providing a polysaccharide or a derivative thereof;
B) oxidizing the polysaccharide or derivative thereof to obtain an oxidized polysaccharide or derivative thereof comprising aldehyde groups, wherein the oxidizing is carried out until an oxidation degree of 0.1% to 80% of the sugar rings in the polysaccharide is obtained;
C) combining the oxidized polysaccharide or derivative thereof with at least one active substance that comprises a primary or secondary amine group in water or a mixture of water and an organic solvent such that the molar ratio of aldehyde groups of the oxidized polysaccharide or derivative thereof to amine groups of the active substance is greater than 1, and allowing the amine groups to react with the aldehyde groups to provide a modified polysaccharide or derivative thereof, without forming nanoparticles;
D) combining the modified polysaccharide or derivative thereof with at least one nanoparticle-forming agent that comprises a primary or secondary amine group in water or a mixture of water and an organic solvent, and allowing the amine groups to react with the aldehyde groups, which reacting of the amine groups with the aldehyde groups produces polysaccharide nanoparticles in an aqueous suspension;

wherein the polysaccharide nanoparticles comprise the oxidized polysaccharide or a derivative thereof, the at least one active substance, and the at least one nanoparticle-forming agent, wherein the at least one nanoparticle-forming agent is selected from the group consisting of:

butylamine, pentylamine, hexylamine, octyloamine, decylamine, dodecylamine, tetradecylamine, hexadecylamine, cyclohexylamine, benzylamine, ethylphenylamine, sphingosines, oleic acid amide, palmitic acid amide, stearic acid hydrazide, palmitic acid hydrazide, oleic acid hydrazide, leucine, isoleucine, valine, methionine, alanine, phenylalanine, cephalin, and amine salts thereof, wherein the at least one active substance is selected from the group consisting of: daunorubicin, doxorubicin, aminoacridins, cisplatin, methotrexate, cytarabine, gemcitabine, dapsone, acyclovir, azidothymidine, 5-fluorouracil, mercaptopurine, imatinib, sunitinib, bleomycin, actinomycin, mitomycin, dactinomycin, melphalan, temozolomide, celecoxib, nelarabine, cladribine, isoniazid, 9-aminoacridine, 4',6-diamidino-2-phenylindole, rhodamine, neutral red, trypan blue, and salts thereof, wherein the polysaccharide is selected from the group consisting of: dextran, starch, starch derivatives, hydroxyethylstarch, amylase, amylase derivatives, cellulose derivatives, hydroxyethylcellulose, hydroxypropylcellulose, carboxymethylcellulose, glycogen, hyaluronic acid, heparin, alginic acid, carrageen, and salts thereof, wherein there are no nanoparticles present in the process until the reacting produces the polysaccharide nanoparticles step D), wherein the only nanoparticles in the aqueous suspension are the polysaccharide nanoparticles created in step D), and wherein the reactions of C) and D) are independently conducted at a solution pH of from 1 to 9 and at a temperature of from 10 to 100 C.

2. The process of claim 1, further comprising:
E) lyophilizing the polysaccharide nanoparticles in an aqueous suspension to provide lyophilized nanoparticles.

3. The process of claim 2, further comprising:
F) resuspending the lyophilized nanoparticles in an aqueous solution.

4. The process of claim 1, wherein the at least one active substance is selected from the group consisting of: daunorubicin, doxorubicin, aminoacridins, cisplatin, methotrexate, cytarabine, gemcitabine, dapsone, acyclovir, azidothymidine, 5-fluorouracil, mercaptopurine, imatinib, sunitinib, bleomycin, actinomycin, mitomycin, dactinomycin, melphalan, temozolomide, celecoxib, nelarabine, cladribine, isoniazid, 9-aminoacridine, acridine dyes, 4',6-diamidino-2-phenylindole, rhodamine, neutral red, trypan blue, and hydrochloride salts thereof.

5. The process of claim 1, wherein the at least one nanoparticle-forming agent is selected from the group consisting of: butylamine, pentylamine, hexylamine, octyloamine, decylamine, dodecylamine, tetradecylamine, hexadecylamine, cyclohexylamine, benzylamine, ethylphenylamine, sphingosines, oleic acid amide, palmitic acid amide, stearic acid hydrazide, palmitic acid hydrazide, oleic acid hydrazide, leucine, isoleucine, valine, methionine, alanine, phenylalanine, cephalin, and hydrochloride salts thereof.

6. The process of claim 4, wherein the at least one nanoparticle-forming agent is selected from the group consisting of: butylamine, pentylamine, hexylamine, octyloamine, decylamine, dodecylamine, tetradecylamine, hexadecylamine, cyclohexylamine, benzylamine, ethylphenylamine, sphingosines, oleic acid amide, palmitic acid amide, stearic acid hydrazide, palmitic acid hydrazide, oleic acid hydrazide, leucine, isoleucine, valine, methionine, alanine, phenylalanine, cephalin, and hydrochloride salts thereof.

7. The process of claim 1, wherein the at least one active substance and the at least one nanoparticle-forming agent are readily soluble salts.

8. The process of claim 7, wherein the readily soluble salts are chosen from hydrochloride, nitrate, and sulfate salts.

9. The process of claim 1, wherein the mixture of water and an organic solvent is a mixture selected from the group consisting of: water/DMSO, water/acetonitrile, and water/ether.

10. The process of claim 1, wherein the polysaccharide or a derivative thereof is selected from the group consisting of: dextran, carboxymethylcellulose, and hyaluronic acid.

11. The process of claim 1, wherein the oxidation in B) is carried out in the presence of periodate ions, salts of lead with the oxidation number of 4, or compounds of copper with the oxidation number of 2.

12. The process of claim 1, further comprising:
E) contacting the polysaccharide nanoparticles with $NaBH_4$ or $NaBH_3CN$ in aqueous solution.

13. The process of claim 1, wherein the at least one active substance is selected from the group consisting of: daunorubicin hydrochloride, doxorubicin hydrochloride, 9-aminoacridine hydrochloride, and cytarabine hydrochloride.

14. The process of claim 1, wherein the at least one nanoparticle-forming agent is selected from the group consisting of: octyloamine hydrochloride, decylamine hydrochloride, dodecylamine hydrochloride, isoleucine hydrochloride, and alanine hydrochloride.

15. The process of claim 1, wherein the polysaccharide nanoparticles consist essential of the oxidized polysaccharide or a derivative thereof, the at least one active substance, and the at least one nanoparticle-forming agent.

16. The process of claim 1, wherein the polysaccharide is selected from the group consisting of: dextran, hyaluronic acid, carboxymethylcellulose and salts thereof.

17. The process of claim 1, wherein the polysaccharide is selected from the group consisting of: dextran, carboxymethylcellulose, carboxymethylcellulose sodium salt, and hyaluronic acid sodium salt.

18. The process of claim 1, wherein the polysaccharide nanoparticle has a mean diameter of at least 72 nm.

19. The process of claim 1, wherein the polysaccharide nanoparticle has a mean diameter of at least 110 nm.

* * * * *